United States Patent
Xie (10) Patent No.: US 12,383,339 B1
(45) Date of Patent: Aug. 12, 2025

(54) AI-ASSISTED SURGICAL MARKING AND INJECTABLE FILLER SYSTEM FOR FACIAL COSMETIC PROCEDURES

(71) Applicant: Alex Xie, West Windsor, NJ (US)

(72) Inventor: Alex Xie, West Windsor, NJ (US)

( * ) Notice: Subject to any disclaimer, the term of this patent is extended or adjusted under 35 U.S.C. 154(b) by 0 days.

(21) Appl. No.: 19/064,387

(22) Filed: Feb. 26, 2025

(51) Int. Cl.
  *A61B 34/10* (2016.01)
  *G06T 19/20* (2011.01)
  *G16H 20/40* (2018.01)

(52) U.S. Cl.
  CPC .............. *A61B 34/10* (2016.02); *G06T 19/20* (2013.01); *G16H 20/40* (2018.01); *A61B 2034/105* (2016.02); *G06T 2210/41* (2013.01)

(58) Field of Classification Search
  None
  See application file for complete search history.

(56) References Cited

U.S. PATENT DOCUMENTS

| | | | | |
|---|---|---|---|---|
| 6,122,541 | A * | 9/2000 | Cosman | A61B 34/20 606/130 |
| 2019/0055832 | A1* | 2/2019 | Peter | E21B 47/01 |
| 2021/0183124 | A1* | 6/2021 | Benditte-Klepetko | A61B 5/167 |
| 2021/0201565 | A1* | 7/2021 | Dibra | G06T 19/00 |
| 2021/0267688 | A1* | 9/2021 | Chacón Quirós | G16H 20/40 |
| 2022/0070385 | A1* | 3/2022 | Van Os | H04N 23/62 |
| 2022/0400310 | A1* | 12/2022 | Dawson | H04N 21/4223 |
| 2023/0038459 | A1* | 2/2023 | Moore | A61B 17/17 |
| 2023/0148425 | A1* | 5/2023 | Donohue | B05B 12/006 118/323 |
| 2023/0260625 | A1* | 8/2023 | Delaet | G16H 20/40 705/2 |
| 2024/0245474 | A1* | 7/2024 | Weiman | A61B 34/25 |
| 2024/0268897 | A1* | 8/2024 | Vyas | G06N 3/084 |

* cited by examiner

*Primary Examiner* — Kyle Zhai
(74) *Attorney, Agent, or Firm* — Walter J. Tencza, Jr.

(57) ABSTRACT

A computing system including at least one computer processor; an artificial intelligence (AI) Engine module including at least one artificial intelligence model; and a computer memory that stores instructions that, when executed by the at least one computer processor, causes the at least one computer processor to perform operations, including: receiving Input Data entered into an Input module by a user; using the AI Engine module to process the Input Data; using the AI Engine module to generate a procedure plan based on the Input Data; generating a visualization of a postoperative patient's face as predicted by the AI Engine module based on the Input Data and the procedure plan generated by the AI Engine module; storing the visualization of the postoperative patient's face in a computer memory; and displaying the visualization of the postoperative patient's face through a Visualization module.

13 Claims, 5 Drawing Sheets

AI-ASSISTED SURGICAL MARKING AND INJECTABLE FILLER SYSTEM FOR FACIAL COSMETIC PROCEDURES

FIELD OF THE INVENTION

This invention pertains to the fields of cosmetic medical procedures and artificial intelligence (hereinafter "AI").

BACKGROUND OF THE INVENTION

Facial cosmetic procedures encompass a range of interventions, including surgeries such as rhinoplasty, blepharoplasty, rhytidectomy (facelift), otoplasty, chin augmentation, lip augmentation, brow lifts, and injectable fillers. Each procedure requires precise planning to achieve optimal aesthetic and functional outcomes.

Surgical markings serve as critical blueprints, guiding surgeons in executing procedures with precision. Traditionally, these markings are manually drawn, relying heavily on the surgeon's expertise and judgment. However, manual markings are subjective and prone to variability, potentially leading to asymmetry, inefficiency during surgery, and suboptimal outcomes. Additionally, they are time-intensive, lack reproducibility, and may not always align perfectly with a patient's unique anatomy or desired aesthetics.

Injectable dermal fillers require accurate placement to enhance facial contours, reduce wrinkles, or restore volume. Achieving desired results with minimal invasiveness necessitates precise injection site determination, accurate filler quantity, and awareness of critical anatomical structures like bone, blood vessels and nerves. The use of lower-gauge needles, which are more susceptible to complications such as puncturing blood vessels or nerves, amplifies these challenges. Variability in injector expertise and anatomical differences further complicate achieving consistent results.

A significant challenge in facial cosmetic procedures lies in the consultation phase. Potential patients are often hesitant to proceed due to uncertainty about the results, leading to prolonged consultations where doctors attempt to explain and visualize potential outcomes. Current methods, such as before-and-after photo comparisons, manual sketches, or static simulations, often fail to capture the dynamic nature of personalized results. This misalignment can lead to dissatisfaction, hesitation, or unrealistic expectations, impacting both patient confidence and procedural outcomes. Advancements in artificial intelligence, particularly in facial recognition and medical imaging, have demonstrated significant promise across various fields. Facial recognition systems use convolutional neural networks (CNNs) to analyze facial features, contours, symmetry, and proportions with high accuracy from images and video. In the medical domain, facial recognition algorithms have been employed to diagnose syndromes, assess facial symmetry, and track changes in facial structures over time. However, most current systems excel at static facial analysis and lack the dynamic, real-time adaptability and responsiveness required in surgical and injectable consultations. In addition, AI solutions tailored to cosmetic applications often fail to incorporate comprehensive datasets, such as demographic variability, medical imaging, and feedback loops, to ensure customization and reliability.

The integration of artificial intelligence (AI) into medical procedures has shown significant promise across various fields, including diagnostics, treatment planning, and robotic surgery. However, its application to surgical markings and dermal fillers, particularly in facial cosmetic surgery, remains underexplored. Current AI solutions for surgery are often limited to image recognition or assisting with intraoperative decision-making, with little focus on preoperative planning tools that assist with consultations or directly impact surgical precision.

SUMMARY OF THE INVENTION

One or more embodiments of the present invention address the application of AI in cosmetic procedures such as facial cosmetic surgery. One or more embodiments of the present invention include apparatuses, systems, and methods for predicting the three dimensional visualization of post-operation results during consultations, generating precise surgical markings for cosmetic surgery, and determining injection points, quantities, and trajectories for injectable fillers such as Botox (trademarked) and hyaluronic acid.

One or more embodiments of the present invention provide a novel AI-assisted system, method, and apparatus designed to enhance the planning and consultations of cosmetic procedures such as facial cosmetic surgery. One or more embodiments may be used in clinical practice such as during consultations and in medical training environments. One or more embodiments may be used in assisting clinical practices by apply markings or plans automatically to a patient's face with minimal surgeon intervention.

In at least one embodiment, a computing system is provided comprising: at least one computer processor; an artificial intelligence (AI) Engine module comprising at least one artificial intelligence model; and a computer memory that stores instructions that, when executed by the at least one computer processor, causes the at least one computer processor to perform operations, including: receiving Input Data entered into an Input module by a user; using the AI Engine module to process the Input Data; using the AI Engine module to generate a procedure plan based on the Input Data; generating a visualization of a postoperative patient's face as predicted by the AI Engine module based on the Input Data and the procedure plan generated by the AI Engine module; storing the visualization of the postoperative patient's face in a computer memory; and displaying the visualization of the postoperative patient's face through a Visualization module.

In a least one embodiment, after the step of generating the visualization of the postoperative patient's face, the at least one computer processor is configured to enable the user to modify the Input Data; and the at least one computer processor is configured to generate a modified visualization of the postoperative patient's face in a computer memory based on the modification of the Input Data.

The at least one computer processor may be configured to enable the user to modify the procedure plan; and to generate a modified visualization of the postoperative patient's face in computer memory based on modification of the procedure plan by the user.

The procedure plan may include surgical markings.

The at least one computer processor may be configured to generate a visualization of a preoperative patient's face with generated surgical markings shown overlaid on top of the preoperative patient's face by use of the AI Engine module.

The modification of the procedure plan by the user may include modification to the surgical markings.

In at least one embodiment, a computing system is provided which includes at least one computer processor; an AI Engine module comprising at least one artificial intelligence model; a computer memory that stores instructions that, when executed by the at least one computer processor, causes the at least one computer processor to perform operations, including: receiving Input Data entered into an Input module by a user; using the AI Engine module to process the Input Data; generating a visualization of a postoperative patient's face as predicted by the AI Engine module based on the Input Data; and displaying a visualization of the postoperative patient's face through a Visualization module.

The at least one computer processor may be configured to generate an alternative visualization of the postoperative patient's face as predicted by the AI Engine module based on the Input Data, and to display the alternative visualization of the postoperative patient's face through the Visualization module.

The at least one computer processor may be configured to generate a further plurality of alternative visualizations of the postoperative patient's face as predicted by the AI Engine module based on the Input Data, and to display the plurality of alternative visualizations of the postoperative patient's face through the Visualization module.

The AI Engine module may be configured to generate a procedure plan based on the Input Data and the visualization of the postoperative patient's face In at least one embodiment, after the AI Engine module generates the visualization of the postoperative patient's face, the at least one computer processor is configured to enable the user to modify the Input Data; and the at least one computer processor is configured to generate a modified visualization of the postoperative patient's face based on modification of the Input Data by the user.

The at least one computer processor may be configured to enable the user to modify the procedure plan; and to generate modified visualization of the postoperative patient's face based on modification of the procedure plan.

The at least one computer processor may be configured to create a visualization of a preoperative patient's face by use of generated surgical markings overlaid on top of the preoperative patient's face as created by the AI Engine module.

In at least one embodiment, a method is provided which includes receiving into a computer processor, Input Data entered into an Input module by a user; using an AI Engine module to process the Input Data; using the AI Engine module to generate a procedure plan based on the Input Data; generating a visualization of a postoperative patient's face as predicted by the AI Engine module based on the Input Data and the procedure plan generated by the AI Engine module; storing the visualization of the postoperative patient's face in a computer memory; and displaying the visualization of the postoperative patient's face through a Visualization module.

In at least one embodiment, after the step of generating the visualization of the postoperative patient's face, the method may include enabling the user to modify the Input Data; and generating a modified visualization of the postoperative patient's face in a computer memory based on the modification of the Input Data.

The method may further include enabling the user to modify the procedure plan; and generating a modified visualization of the postoperative patient's face in a computer memory based on modification of the procedure plan by the user.

The procedure plan may include surgical markings.

The method may further include generating a visualization of a preoperative patient's face with generated surgical markings shown overlaid on top of the preoperative patient's face by use of the AI Engine module.

The method may further include generating a visualization of a preoperative patient's face with surgical markings shown overlaid on top of the preoperative patient's face by use of the AI Engine module; wherein modification of the procedure plan by the user includes modification to the surgical markings.

In at least one embodiment of the present invention, a method is provided which may include receiving at a computer processor, Input Data entered into an Input module by a user; using an AI Engine module to process the Input Data; generating a visualization of a postoperative patient's face as predicted by the AI Engine module based on the Input Data; and displaying a visualization of the postoperative patient's face through a Visualization module.

The method may further include generating an alternative visualization of the postoperative patient's face as predicted by the AI Engine module based on the Input Data, and displaying the alternative visualization of the postoperative patient's face through the Visualization module.

The method may further include generating a further plurality of alternative visualizations of the postoperative patient's face as predicted by the AI Engine module based on the Input Data, and displaying the plurality of alternative visualizations of the postoperative patient's face through the Visualization module.

The AI Engine module may be configured to generate a procedure plan based on the Input Data and the visualization of the postoperative patient's face.

In at least one embodiment, after the AI Engine module generates the visualization of the postoperative patient's face, the method may include enabling the user to modify the Input Data; and generating a modified visualization of the postoperative patient's face through the Visualization module, based on modification of the Input Data by the user.

The method may further include enabling the user to modify the procedure plan; and generating a modified visualization of the postoperative patient's face based on modification of the procedure plan.

The method may further include creating a visualization of a preoperative patient's face by use of generated surgical markings overlaid on top of the preoperative patient's face as created by the AI Engine module.

After the step of generating the visualization of the postoperative patient's face, the at least one computer processor may be configured to enable the user to modify the postoperative patient's face; and wherein the at least one computer processor is configured to generate a modified procedure plan based on the modification of the postoperative patient's face.

In at least one embodiment, after the AI Engine module generates the visualization of the postoperative patient's face, the at least one computer processor is configured to enable the user to modify the postoperative patient's face; wherein the at least one computer processor is configured to generate a modified procedure plan based on the modification of the postoperative patient's face.

In at least one embodiment, after the step of generating the visualization of the postoperative patient's face, the method may include enabling the user to modify the postoperative patient's face; and generating a modified procedure plan based on the modification to the postoperative patient's face.

After the AI Engine module generates the visualization of the postoperative patient's face, the method may include enabling the user to modify the postoperative patient's face; and generating a modified procedure plan based on the modification of the postoperative patient's face.

DETAILED DESCRIPTION OF THE INVENTION

Figure 1:
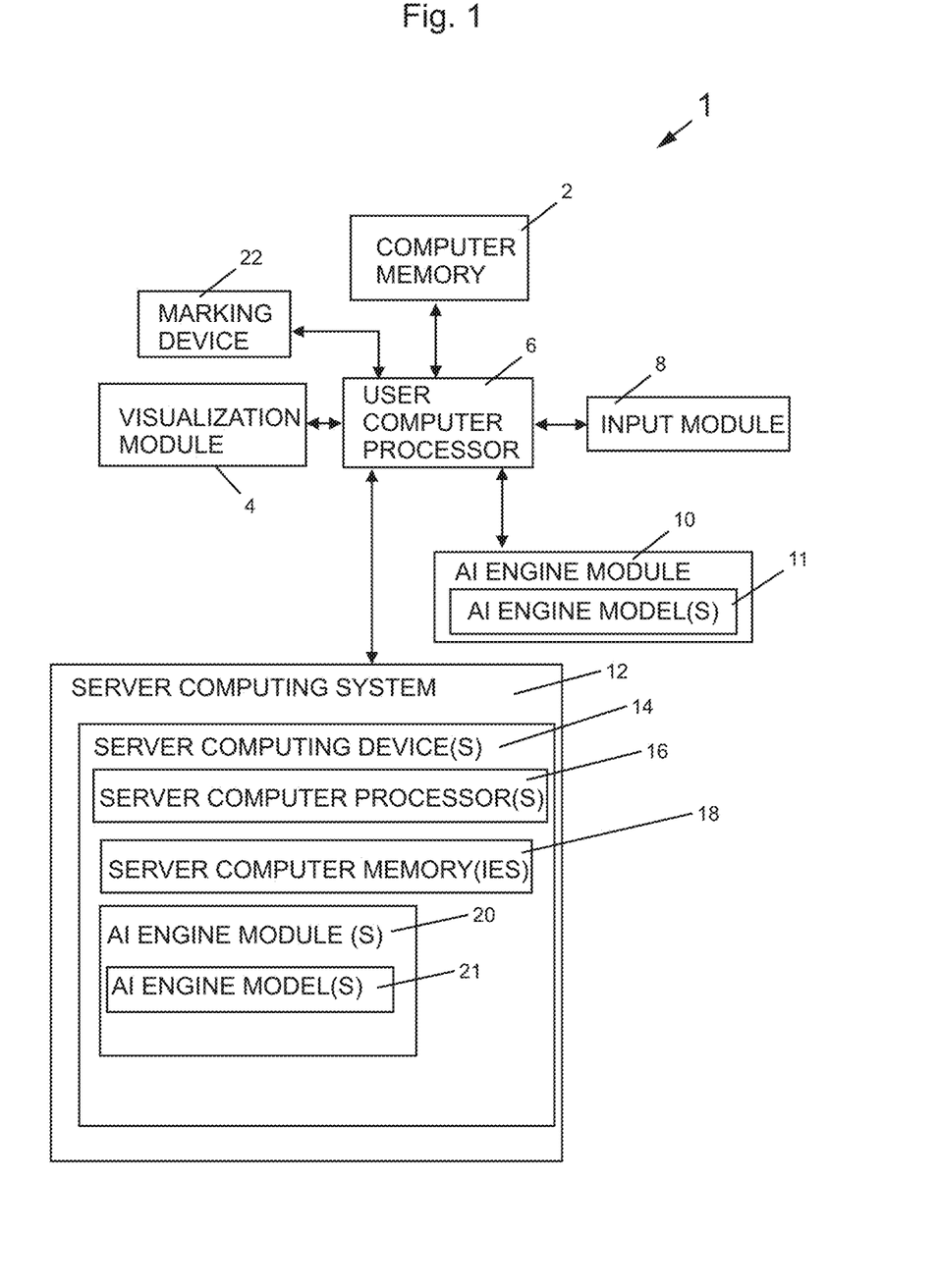
FIG. 1 is a simplified block diagram of components of a system, method, and/or apparatus of at least one embodiment of the present invention.

FIG. 1 is a simplified block diagram 1 of components of a system, method, and/or apparatus of at least one embodiment of the present invention.

The components in block diagram 1 includes computer memory 2, Visualization module 4, a user computer processor 6, Input module 8, Artificial Intelligence (hereinafter "AI") Engine module 10, optionally, server computing system 12, and marking device 22. The server computing system 12 includes one or more server computing device(s) 14 each of which includes one or more server computer processor(s) 16, one or more server computer memories 18, and one or more AI Engine module(s) 20. Each of the one or more AI Engine module(s) 20 may include one or more AI Engine model(s) 21. Each of the one or more AI Engine module(s) 10 may include one or more AI Engine model(s) 11.

The computer memory 2 and 18 may be any form of computer and/or electronic memory.

Each of the Visualization module 4, the Input module 8, the AI Engine module 10, and the AI Engine module 20 may include or may be computer software which is stored in computer memory 2 and/or 18, and/or some other computer memory, and which is implemented by the user computer processor 6 and/or server computer processor 16.

The Input module 8, may be, or may include, for example, a computer, phone or tablet touch screen, a computer keyboard, a three dimensional scanner, camera or other such image or video capturing device, and/or a computer mouse.

Figure 2A:
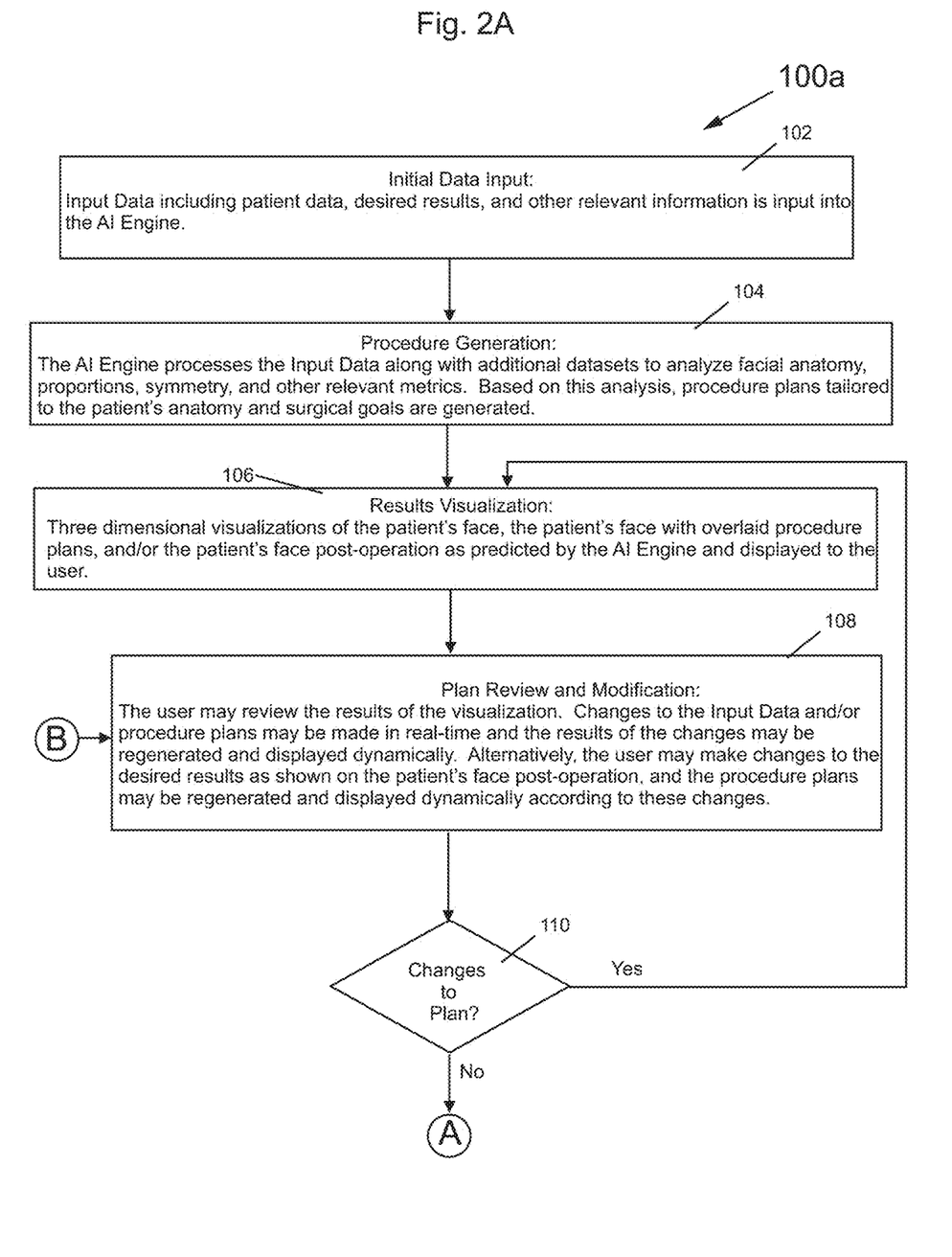
FIG. 2A is a first part of a flow chart of a first method or process in accordance with at least one embodiment of the present invention.

FIG. 2A is a first part 100a of a flow chart of a first method or process in accordance with at least one embodiment of the present invention.

At step 102, Input Data which may include at least one of the following: patient data including the type of surgery, media such as images or videos, medical imaging, patient information, demographics and medical history, and desired results are input into the Input module 8 for transfer into the AI Engine module 10 and/or 20 as implemented by the computer processor 6 and/or 16 in accordance with computer programming stored in computer memory 2 and/or 18.

At step 104, the AI Engine module 10 is programmed to process the Input Data provided from step 102, along with additional datasets to analyze facial anatomy, proportions, symmetry, and other relevant metrics. Based on this analysis, precise surgical markings, injection plans or procedure plans tailored to the patient's anatomy and procedure goals are generated by the AI Engine module 10, in accordance with computer software stored in AI Engine module 10 and/or computer memory 2 as implemented by AI Engine module 10 and/or user computer processor 6.

At step 106 three dimensional visualizations are generated of the patient's face, the patient's face with overlaid surgical markings, injection plans or procedure plans, and/or the patient's face post-operation as predicted by the AI Engine module 10 and/or Visualization module 4 as programmed by computer software stored in module 4 and/or computer memory 2, and implemented by module 4 and/or user computer processor 6.

In at least one embodiment, step 106 may occur before step 104. In this embodiment, at step 106, the AI Engine module 10 is programmed to process the Input Data provided from step 102, along with additional datasets to analyze facial anatomy, proportions, symmetry, and other relevant metrics. Based on this analysis, three dimensional visualizations are generated of the patient's face and/or the patient's face post-operation as predicted by the AI Engine module 10 and/or Visualization module 4 as programmed by computer software stored in module 4 and/or computer memory 2, and implemented by module 4 and/or user computer processor 6.

Subsequently, at step 104, the AI Engine module 10 is programmed to process the Input Data provided from step 102, the predicted patient's face in step 106, and additional relevant datasets. Based on this analysis, precise surgical markings, injection plans or procedure plans tailored to the patient's anatomy and procedure goals are generated by the AI Engine module 10 in order to achieve the results as shown in the predicted patient's face in step 106, in accordance with computer software stored in AI Engine module 10 and/or computer memory 2 as implemented by AI Engine module 10 and/or user computer processor 6.

At step 108, plan review and modification take place. The user may review the results provided by the Visualization module 4 at step 106. The visualization module 4 may include a monitor such as a computer monitor and/or tablet or phone display.

The Input module 8 and/or computer software for the Input module 8 is configured to allow a user to make changes to the Input Data and surgical marking, injection plans, or procedure plans in real-time by the user through the Input module 8 and the results of the changes are configured to be regenerated and displayed dynamically by the Visualization module 4.

Alternatively, one or more embodiments of the present invention permit a user to make changes in real-time to the desired results as shown on the patient's face post-operation, and the surgical marking, injection plans, or procedure plans are configured to be regenerated and displayed dynamically by the Visualization module 4 according to the changes in the desired results.

As indicated by Step 110, if the user has made changes to the plan and/or the desired results, then the procedure loops back to step 106.

Figure 2B:
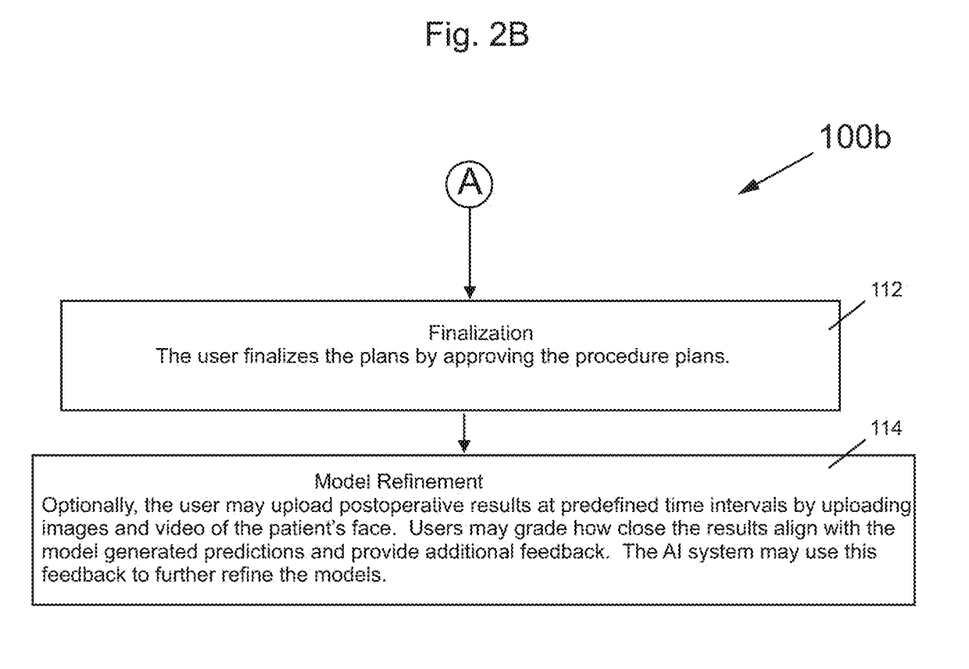
FIG. 2B is a second part of the flow chart of the first method.

If the user intends to finalize plans, at step 110, then the procedure next flows to node A, which flows to step 112 on flow chart part 100b, shown in FIG. 2B.

At step 112, the user is able to finalize plans by approving surgical markings, injection plans or procedures plans, such as by user input into the Input module 8, in accordance with computer software, for example, stored in the Input module 8, and/or in the computer memory 2.

At step 114, the Input module 8 and/or the computer memory 2 is optionally programmed with computer software to allow a user to upload postoperative results at predefined time intervals such by uploading images and/or video of the patient's face immediately after surgery, one week after surgery, and one to three months after surgery. The Input module 8 and/or the computer memory 2 is optionally programmed to allow users to grade how close the results align with the AI model generated predictions provided by the AI Engine module 10 and provide additional feedback to the AI Engine module 10, through the Input module 8. The AI Engine module 10 may be programmed by computer software to use this feedback to further refine the models.

Figure 3:
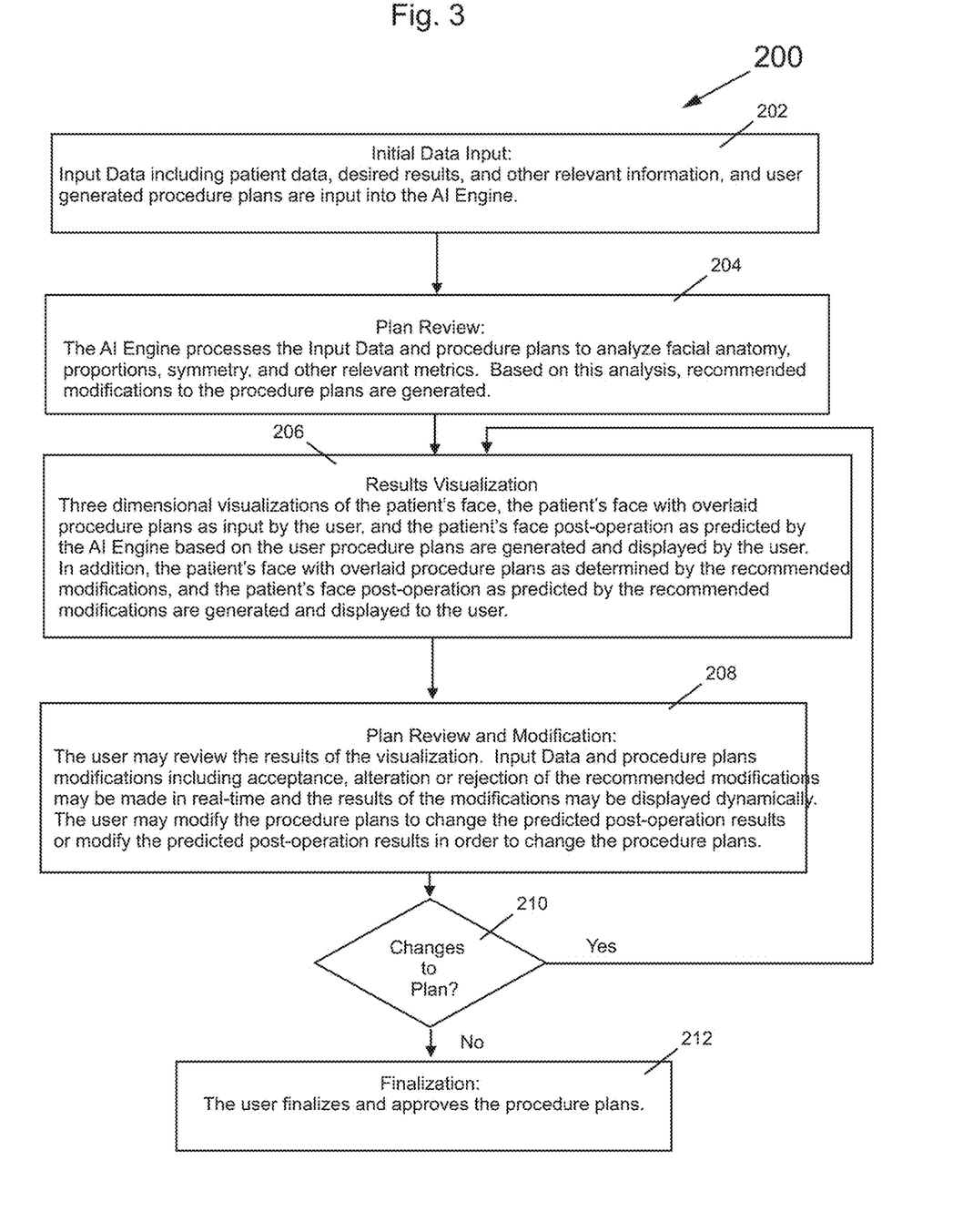
FIG. 3 is a flow chart of a second method or process in accordance with at least one embodiment of the present invention.

FIG. 3 is a flow chart 200 of a second method or process in accordance with at least one embodiment of the present invention.

At step 202, Input Data which may include at least one of the following: patient data including the type of surgery, media such as images or videos, medical imaging, patient information, demographics and medical history, and desired results are input into the AI Engine module 10 using the Input module 8, as implemented by the user computer processor 6 in accordance with computer programming stored in computer memory 2. The AI Engine module 10 and/or the Input module 8, in at least one embodiment are further programmed by computer software to receive additional information input such as manually generated surgical markings, injection plans or procedure plans.

At step 204, the AI Engine module 10 is programmed to process the data provided from step 202, and user inputs of manual markings, injection plans or procedure plans to analyze facial anatomy, proportions, symmetry, and other relevant metrics. Based on this input and analysis by the AI Engine module 10, as programmed by computer software, recommended modifications to the manual markings or plans are generated by the AI Engine module 10.

At step 206 three dimensional visualizations of the patient's face, the patient's face with overlaid surgical markings, injection plans or procedure plans, as input by the user through Input module 8, and/or the patient's face post-operation as predicted by the user input surgical markings, injection plans or procedure plans are generated by the AI Engine module 10, in accordance with computer programming, and displayed to the user by Visualization module 4. In addition, the patient's face with overlaid surgical markings, injection plans or procedure plans as determined by the AI Engine module 10, in accordance with computer programming, and recommended modifications, and the patient's face post-operation as predicted by the recommended modifications are generated by the AI Engine module 10 are displayed to the user by Visualization module 4 in accordance with computer programming.

At step 208 plan review and modification takes place. The user may review the results provided by using the Visualization module 4 at step 206. The Visualization module 4 may include a computer monitor.

Input Data from the user provided through Input module 8 and surgical markings, injection plans or procedure plans modifications including acceptance, alteration or rejection of the AI recommended modifications, provided by AI Engine module 10, in at least one embodiment, are configured to be made in real-time and the results of the modifications are configured to be displayed dynamically using the Visualization module 4.

In at least one embodiment, computer software is provided, such as for the AI Engine module 10 and/or the user computer processor 6, which allows the user to modify the surgical markings, injection plans or procedure plans to change the predicted results by use of the Input module 8, or modify the predicted results by use of the Input module 8, in order to change the surgical markings, injection plans or procedure plans.

As indicated by Step 210, if the user has made changes to the plan then the procedure loops back to step 206.

If the user intends to finalize plans, at step 210, then the procedure next flows to step 212 shown in FIG. 3.

At step 212, in at least one embodiment, the user can finalize plans by approving the surgical markings, injection plans or procedure plans by providing Input Data to the Input module 8, which is then processed by the user computer processor 6 and an indication of approval is stored in computer memory 2, and/or displayed on a computer monitor of Visualization module 4.

Figure 4:
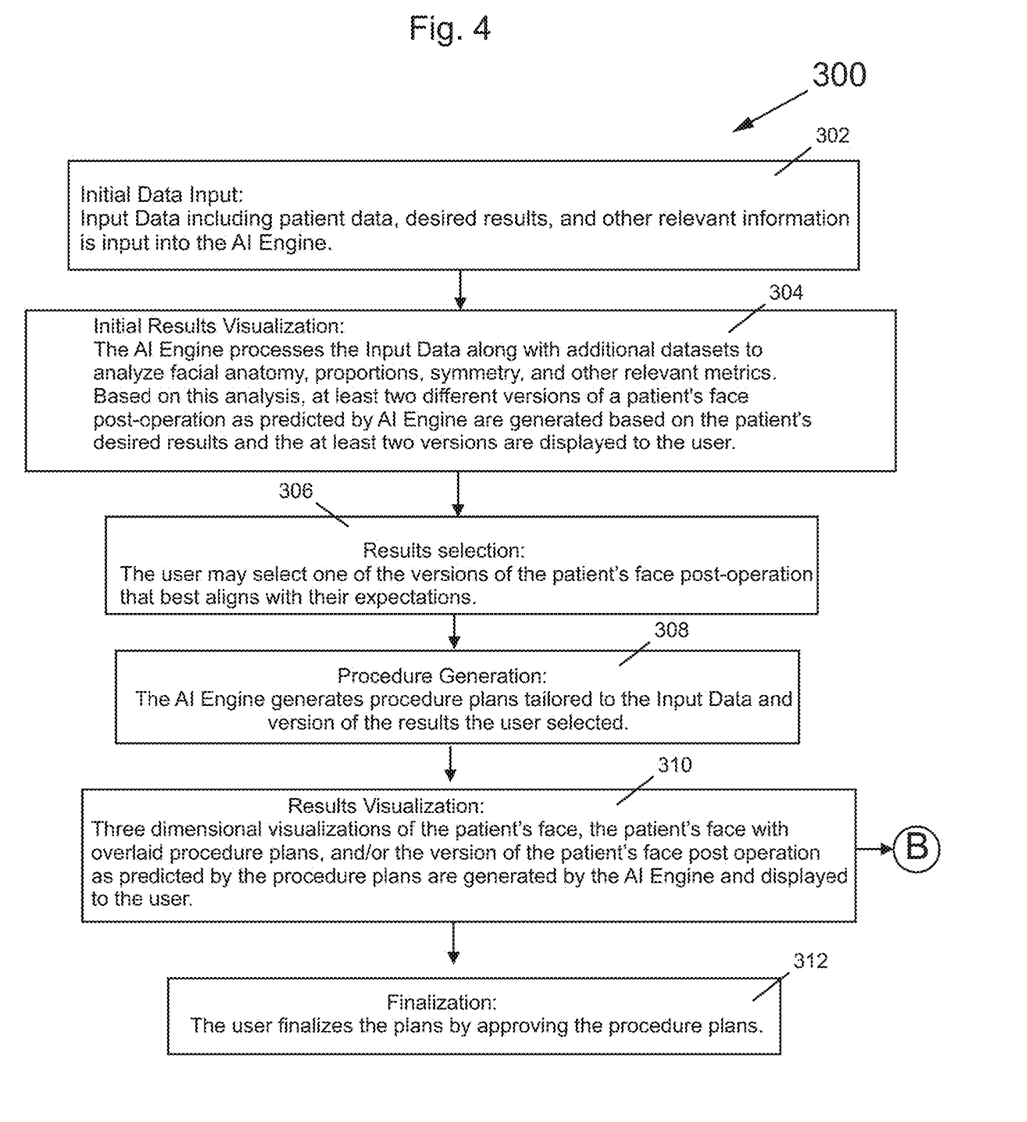
FIG. 4 is a flow chart of a third method or process in accordance with at least one embodiment of the present invention.

FIG. 4 shows a flow chart 300 of a third method or process in accordance with at least one embodiment of the present invention.

At step 302, Input Data which may include at least one of the following: patient data including the type of surgery, media such as images or videos, medical imaging, patient information, demographics and medical history, and desired results are input into the Input module 8 for transfer into the AI Engine module 10 as implemented by the user computer processor 6 in accordance with computer programming stored in computer memory 2.

At step 304, the AI Engine module 10 is programmed to process the Input Data provided from step 302, along with additional datasets to analyze facial anatomy, proportions, symmetry, and other relevant metrics. Based on this analysis, at least two different three dimensional visualization versions of the patient's face post-operation as predicted by the AI Engine module 10 are generated based on the patient's desired results and the at least two versions are displayed to the user. The AI Engine module 10 may provide a number of alternative visualizations of the patient's face post-operation based on factors including but not limited to model training based on previous procedures, user input desired results, feasibility of the procedure and risk factors based in part on the Input Data.

At step 306, the user computer processor 6 and/or the AI Engine modules 10 and/or 20 are programmed to allow, the user to select one of the versions of the patient's face post-operation to proceed. The version selected typically is the version that best aligns with the patient's expectations considering results, risk factors, feasibility, recover time, and any other such factors.

At step 308, the AI Engine module 10 and/or 20 is programmed to process the Input Data provided from step 302, along with additional datasets to analyze facial anatomy, proportions, symmetry, other relevant metrics, and version selected in step 306 to generate precise surgical markings, injection plans or procedure plans that will achieve the results shown in the version selected. Optionally, the generation of the surgical markings, injection plans or procedure plans may occur at step 304 for each version of the patient's face post-operation shown, prior to the user selecting one of the versions. At step 308 the AI Engine module 10 and/or 20 is programmed to generate procedure plans and to store these plans in computer memory, such as memory 2, and/or display on visualization module 4. The AI Engine module 10 and/or 20 is programmed to generate these procedure plans based on and/or tailored to the Input Data and the version of the results that the user has selected through Input module 8.

At step 310, optionally, three dimensional visualizations of the patient's face, the patient's face with overlaid surgical markings, injection plans or procedure plans, and/or the patient's face post-operation are generated by the AI Engine module 10 and/or 20 and stored in computer memory 2 and/or displayed on visualization module 4, in accordance with programming for the AI Engine module 10 and/or 20. These three dimensional visualizations are predicted by the AI Engine module 10 and/or 20 in accordance with programming for the AI Engine module 10 and/or 20, based on the surgical markings, injection plans or procedure plans, and these three dimensional visualizations are generated by the AI Engine module 10 and/or 20 and stored in computer memory 2 and/or displayed to the user by the visualization module 4 in accordance with programming of the AI Engine modules 10 and/or 20.

Optionally, the procedure may next flow from step 310 to node B, which flows to step 108 on flow chart part 100*a*, shown in FIG. 2A.

Otherwise, at step 312, one or more of the computer processor 6, and/or the AI Engine modules 10 and/or 20 are programmed to allow the user to be able to finalize plans by approving surgical markings, injection plans or procedures plans, such as by user input into the Input module 8, in accordance with computer software, for example, stored in one or more of the Input module 8, the computer memory 2, and/or the AI Engine modules 10 and/or 20.

One or more embodiments of the present invention include a process executed by one or more computer processors and/or AI Engine modules 10 and/or 20, comprising the following steps:

(1) Patient Data Acquisition: Input of Input Data through Input module 8 which may include at least one of the following: the desired procedure and patient-specific data such as 3D facial scans, media such as photographs or videos, medical imaging (e.g., CT scans, MRI, X-rays, ultrasounds etc.), demographics (age, sex, race, etc.), medical history including previous surgeries, allergies, drug use, and other relevant factors such as risk factors, recovery time preference, height, weight, body fat percentage, and patient desired results. Desired results may be input as specific amounts of tissue removal at particular points, length measurements between points or degree of repositioning, volume or mass to be added or subtracted from specific locations, or description of desired end results such as facial symmetry or reduced wrinkles. As an example, in upper blepharoplasty, the input may consist of patient's desire to remove excess skin and fat from the upper eyelids. This can be input as numerical values such as area or volume of skin or fat to remove from specific regions, or generalized desired outcome of the surgery such as removal of a double eyelid or desired symmetry between eyes. The Input Data may be pre-processed by standardizing the collected data and making sure the formatting is consistent. Image processing techniques may be used to enhance, segment, and extract key elements from input media such as images or videos.

(2) Integration of various AI models, such as by one or more of AI Engine module 10 and/or 20, to analyze patient-specific data such as the patient's facial anatomy including distribution of skin, muscle, and fat, evaluation of key indicators such as facial proportions, symmetry, and skin elasticity, and desired results. Additional information to be analyzed may include datasets such as facial recognition of other members of the patient demographics, procedure plans such as surgical markings and injection plans, results of previously performed procedures, relevant anatomic models such as bone, blood vessel and nerve mapping, and default results criteria based on the procedure selected.

(3) Automatic generation of procedure plans, in accordance with computer programming, such as by AI Engine module 10 and/or 20, such as precise surgical markings, injection plans, or procedure plans tailored to the patient's unique facial anatomy and the desired outcomes. Multiple alternative plans may be generated by the AI Engine modules 10 and/or 20 and stored in computer memory 2, and displayed on visualization module 4, for user consideration based on risk factors, feasibility, recovery time, and expected results. For example, medical imaging of the patient may be used as part of the Input Data which the AI Engine module 10 may consider in generating procedure plans that avoid damaging critical anatomical features such as bone structure, blood vessels, or nerves by adjusting injection location, angle, depth and needle gauge and alternative plans may be generated based in part on the user's risk tolerance or recovery time.

(4) Generation of 3D visualizations of the patient's face, such as through Visualization module 4, by one or more of computer processor 6, AI Engine modules 10 and/or 20, in accordance with computer software programming, and/or visualization of the patient's face with overlaid procedure plans such as surgical markings and/or injection plans, and the post-operative patient's face as predicted by the procedure plans such as surgical markings and/or injection plans. In at least one embodiment, multiple versions of the post-operative patient's face may be generated based on AI Engine 10 and/or 20 training in part on previous procedures, risk factors, feasibility, recover time, patient desired results and any other such factors. In at least one embodiment the visualization of step (4) may be generated prior to the procedure plans.

(5) A user interface (UI), such as including Input module 8 and/or Visualization module 4, that allows users to review, adjust, and approve the AI-generated procedure plans such as surgical markings or injection plans, and/or in combination with AI Engine module 10 and/or 20 in accordance with computer software programming. In at least one embodiment, users may be able adjust Input Data or make modifications to the procedure plans such as the surgical markings and/or injection plans, through input module 8, in accordance with software programming in computer processor 6, and/or AI Engine Modules 10 and/or 20, in order to achieve the desired results. In at least one embodiment, users may be able to view and adjust alternative plans generated by AI Engine module 10 and/or 20, and displayed on Visualization module 4, and/or stored in computer memory 2, based on risk factors, desired results, or other such factors.

(6) In at least one embodiment, dynamic feedback capabilities, are provided, such as through Input module 8, Visualization module 4, and AI Engine modules 10 and/or 20, that enable real-time regeneration of realistic results on Visualization module 4 and/or in computer memory, such as computer memory 2, based on user changes. When users modify Input Data or surgical, injection, or procedure plans, through visualization module 4, and/or in computer memory 2, the system, including one or more of AI Engine modules 10 and/or 20, is programmed to recalculate and update the visualization in real-time in computer memory 2 and to display on Visualization module 4, to reflect the new parameters, ensuring the plan remains precise and adaptable and providing immediate feedback in response to the changing inputs.

(7) Once satisfied, the plans are finalized and saved in computer memory, such as computer memory 2, of the system.

(8) Optionally, ability to scan a user's procedure plans such as manual surgical markings via photo or video, such as through Input module 8, analyze the Input Data, such as by AI Engine module 10 and/or 20, provide visualization of the predicted results, such as by Visualization module 4, and suggest improvements to the procedure plans such as surgical markings such as through visualization module 4 and/or as stored in computer memory 2. Alternatively, the ability for a user to input through Input module 8, procedure plans such as injection plans including placement, depth, and volume via UI or photo or video, analyze the input data, provide visualization through Visualization module 4, of the results, and suggest improvements to the procedure plans such as injection plans via AI Engine modules 10 and/or 20.

(9) Optionally, in at least one embodiment, any one of Input module 8, computer processor 6, AI Engine modules 10 or 20 may be programmed by computer software to allow postoperative results to be uploaded by means of Input module 8 to AI Engine module 10 or 20, at defined time intervals such as immediately after surgery, one week after surgery, and three months after surgery to further refine the AI model of the AI Engine module 10 and/or 20. In at least one embodiment, the AI Engine modules 10 or 20 are programmed to record results, in computer memory 2 in the form of photographs, videos, 3D facial scans, and medical imaging or as numerical values. In at least one embodiment, users are able grade, through programming of AI Engine module 10 and/or 20, and/or by using Input module 8, how close the results align with the model-generated predictions, provide specific feedback on any deviation, and document in computer memory 2, extenuating circumstances that may have affected outcomes.

(10) Optionally during steps (5) or (6), the computer processor 6 and/or AI Engine modules 10 and/or 20 may be programmed with computer software to allow a user, through Input module 8, to adjust the AI-generated results provided by AI Engine module 10, of the post-operative patient's face in order to regenerate an image of the patient's face with procedure plans such as surgical markings or injection plans overlaid, on the Visualization module 4, in accordance with programming of the computer processor 6 and/or AI Engine modules 10 and/or 20. The adjustments may be made by interacting with the Input module 8, to change numerical values associated with various actions and regions of the procedure, or visually, through Visualization module 4, such as by selecting actions and clicking and dragging regions of the face or a slider bar using a mouse on a computer or using a finger on a tablet. In at least one embodiment, procedure plans are dynamically updated in real-time, in computer memory 2, in accordance with computer programming of the computer processor 6 and/or AI Engine modules 10 and/or 20, based on the user's modifications (which in at least one embodiment are stored in computer memory 2) to the generated results of the post-operative patient's face. In at least one embodiment, any user changes to the procedure plans or post-operative patient's face and resulting changes to the AI Engine 10 generated post-operative patient's face or procedure plans may be saved such as in computer memory 2 for recall and visualization such as for use in side-by-side comparisons.

(11) Optionally, the system may allow for multi-user collaboration, such as between a patient and doctor in which multiple users may jointly generate, review and modify parts of the system.

(12) Optionally, in at least one embodiment the marking device 22 is configured to mark or draw the procedure plans such as surgical markings or injection plans on the actual patient's face based on the procedure plans generated by the AI Engine 10 and/or 20. The marking device 22 may be a robotic arm or similar device that may automatically apply the procedure plans such as by directing a Sharpie without user or surgeon intervention, in accordance with software programming of the user computer processor 6, and/or AI engine modules 10 and/or 20. Alternatively, the marking device 22 may be configured to apply the markings by means of projecting light or laser(s) directly onto the patient's face. This marking device 22 may be used at any point during the process after the procedure plans are generated.

One or more embodiments of the present invention may use one or more computer software modules or components, which are stored in computer memory and are executed by a computer processor. The one or more computer software modules may include (a) the AI Engine computer software module 10 and/or 20, (b) the Input computer software module 8, and (c) the Visualization computer software module 4.

(a) The AI Engine computer software module 10 and/or 20, in at least one embodiment, is programmed by computer software to:

(i) Utilize various types of AI models to generate surgical, injection or procedure plans based in part on user input information.

(ii) Utilize facial recognition models to identify, map and extract relevant biometric data such as measurements and patient specific conditions.

(iii) Utilize generative AI models to generate realistic three dimensional models of a patient's face in real-time. The generative AI model may obtain information from the AI and facial recognition models to generate the pre-operative patient's face, the pre-operative patient's face with surgical or injection plans overlaid, and the predicted post-operative patient's face.

(iv) AI models, facial recognition systems, and generative AI models are used in combination to accurately capture Input Data including patient data, predict best surgical markings, injection plans, procedure plans, and procedure outcome, and generate various realistic models of the patient's face. Additional datasets such as anatomical models, best practices, previous patient results, etc. may be used in combination with Input Data or as a part of the training of the AI Models. In addition, the system allows for real-time visualization of the predicted results in response to user modifications to the input values, surgical, injection or procedure plans, and user desired results. The models used may include neural networks such as convolutional neural networks, machine learning such as supervised, unsupervised and deep learning, decision trees, generative AI, regression models, classifier models, and/or other such models, algorithms, and training techniques. The models may be trained on layers of comprehensive datasets including anatomical models, prior surgical and filler procedures and outcomes including media such as images or video of the patient before surgery and at various time intervals after surgery, surgical markings, injection plans, procedure plans, desired and satisfaction with results, genetics, demographics, and various other pertinent medical information. The models may be used independently or in conjunction with other models in sequential layers or in parallel.

(v) Optionally, one or more models of the AI Engine module 10 may be stored and trained on the server computing system 12 that communicates with the user computer processor 6. The server computing system 12 may include one or more server computing devices 14, where each may have a server computer processor 16, server computer memory 18 and AI Engine module 20. The server computing system 12 may receive information such as through the Input module 8 from the user computer processor 6 in order to run models, and communicate outputs to the user computer processor 6. In this manner the necessary computing power may be transferred from the user computer processor 6 to the server computing system 12.

(b) The Input computer software module 8, in at least one embodiment, is programmed by computer software to:
  (i) Accept desired procedure and Input Data including patient data, including 3D facial scans, photographs, videos, medical imaging (e.g., CT scans, MRI, X-rays, etc.), demographics (age, sex, race, etc.), medical history, and other relevant factors such as height, weight, body fat percentage, and patient desired results. Desired results may be input as specific amounts of tissue removal at particular points, length measurements between points or degree of repositioning, volume or mass to be added or subtracted from specific locations, or description of desired end results.
  (ii) Have an ability to integrate real-time data input, such as video scans during consultations.

(c) The Visualization computer software module 4, in at least one embodiment is programmed by computer software to:
  (ii) Provide detailed, real-time 3D visualizations of the patient's face, the patient's face with overlaid surgical markings and/or injection or procedure plans generated by the AI Engine module 10, and the post-operative patient's face as predicted by the Ai Engine module 10.
  (ii) Optionally overlay additional information such as critical anatomical features, such as bone structure, blood vessels and nerves, to guide safe execution and achieve the desired results.
  (iii) Allow for real-time visualization of changes to any inputs or modifications to the suggested surgical markings and/or injection or procedure plans, and user desired results.

Example Use Case in Blepharoplasty:

A user may input Input Data including their specific patient data and demographics for an upper blepharoplasty procedure, through Input module 8, indicating a desire to remove a generalized amount of excess skin from their upper eyelids. Hidden features such as the eyelid skin crease is an essential part of blepharoplasty, and manipulation of the eyelids may be necessary to provide better views during imaging or capturing video in order to provide the AI system with enough information to provide a complete analysis.

The system such as through AI Engine module 10 is programmed by computer software and/or configured analyze the images and video of the patient's face, noting various examination measurements and criteria for different parts of the eye and surrounding region. For example, ptosis, symmetry or lack thereof between eyelids and brows, amount and thickness of excess skin, inflammation, skin lesions, and various other conditions are identified and considered. Demographic specific features such as epiblepharon in Asians may also be identified. Default values may be initially used to generate surgical markings and postoperative facial image. For example, the ratio between the tarsal platform to the distance between the upper lid crease and brow should be 1:1.618, or the Golden ratio, and the corneal reflex-lid margin distance in Caucasians should measure between 3.5 to 4 mm (millimeters) and be symmetrical. These default measurements may be overridden by an advanced user such as a surgeon during data input.

Interactive models of the patient's face, the patient's face with surgical markings overlaid, and the post-operative patient's face as predicted by the surgical markings is generated by AI Engine module 10 in accordance with computer programming. In at least one embodiment, the Input module 8 is programmed to permit a user to change the numerical values associated with the procedure plan or each individual surgical marking, and the AI Engine module 10 is programmed and/or configured to regenerate the surgical markings and expected results in real-time, and to display them through the Visualization module 4. Alternatively, the user may interactively manipulate, through the Input module 8 and/or the Visualization module 4, the surgical markings and the numerical values and expected results are regenerated in real-time.

Alternatively, the AI Engine module 10 may generate one or various visualization of the patient's post-operative patient's face based on various factors such as results of previous procedures of similar demographics, risk factors, etc. For example, the AI Engine model 10 may recognize that the patient is Asian and has epiblepharon and generate a version of the visualization that corrects this, without the patient specifically mentioning the condition or inputting correcting for it in the input desired results. The procedure plan(s) may be generated before or after the visualization(s) are generated.

Once the user is satisfied with the surgical markings and results, the plan is finalized, and an indication that the plan is finalized is configured to be stored in computer memory, such as computer memory 2. The procedure plans may be sent to a marking device 22 which may be used to mark or draw the procedure plans on the patient's face based on the procedure plans generated by the AI Engine. The marking device 22 may be a robotic arm or similar device that may automatically apply the procedure plans such as by directing a Sharpie without user or surgeon intervention. Alternatively, the marking device 22 may apply the markings by means of projecting light or laser(s) directly onto the patient's face.

After the procedure, additional information may be uploaded such as images and video of the patient at designated time periods post-operation. In at least one embodiment, the system and/or Input module 8 is programmed to allow the user to grade the results of the AI generated results from the AI Engine module 10, in comparison to actual results and provide feedback on patient and procedure specific factors that occurred during surgery and recovery. This information may be added to the AI Engine module 10 and/or to computer memory 2, for further refinement in future use.

In at least one embodiment, the AI Engine module 10 is programmed by computer software to continually scan the patient's face via video to refine the input data dynamically in response to additional information collected from the patient such as changes in posture, expression or physical manipulation such as lifting eyelids, while the user is interacting with the system. This feature allows for real-time updates to the suggested surgical markings or injection plan and the visualization of expected outcomes, enhancing accuracy and adaptability. In addition, the AI generated model by the AI Engine module 10 is programmed by computer software to mirror the patient's face in real time, changing the displayed posture, expression or facial positioning based on the patient's movement. Real-time adaptability ensures the system remains responsive to surgeon or patient-driven modifications, creating a seamless, interactive planning experience.

In at least one embodiment, the procedures are not limited to facial cosmetic surgery. The procedures may assist in a variety of surgical procedures such as orthopedics or general surgery. For any such procedure, references to specific anatomical regions such as face or facial may be replaced by the equivalent relevant anatomical region such as knee for knee replacement surgery, breast for cosmetic breast surgery, or head for neurosurgery, for example.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. A computing system comprising:
at least one computer processor;
an artificial intelligence (AI) Engine module comprising at least one artificial intelligence model;
a computer memory that stores instructions that, when executed by the at least one computer processor, causes the at least one computer processor to perform operations, including:
receiving Input Data entered into an Input module by a user;
using the AI Engine module to process the Input Data;
using the AI Engine module to generate a first procedure plan based on the Input Data and the at least one artificial intelligence model;
generating a first visualization of a predicted postoperative face of a patient as predicted by the AI Engine module based on the Input Data and the first procedure plan generated by the AI Engine module;
storing the first visualization of the predicted postoperative face of the patient, in a computer memory;
displaying the first visualization of the predicted postoperative face of the patient through a Visualization module; and
after the first procedure plan is executed on a preoperative face of the patient to form an actual postoperative face of the patient, receiving postoperative feedback from the patient at the AI Engine Module;
wherein the postoperative feedback includes grading from the patient as to how close the predicted postoperative face of the patient is to the actual postoperative face of the patient;
and wherein the AI Engine module uses the post postoperative feedback to refine the at least one artificial intelligence model.

2. The computing system of claim 1 wherein
the computer memory that stores instructions, includes instructions that, when executed by the at least one computer processor, causes the at least one computer processor to perform operations, including:
receiving facial recognition Input Data for a preoperative face of a patient in real-time, said facial recognition Input Data captured by a facial recognition system, said facial recognition Input Data including changes based on movement of the patient;
using the AI Engine module to process the facial recognition Input Data;
using the AI Engine module to generate the first procedure plan and a second procedure plan based on the facial recognition Input Data;
generating the first visualization and a second visualization of a postoperative face of the patient as predicted by the AI Engine module based on the facial recognition Input Data and the first procedure plan and the second procedure plan, respectively, generated by the AI Engine module, wherein the first visualization and the second visualization are updated in real time based on movement of the patient;
storing the first visualization and the second visualization of the postoperative face of the patient, as updated in real time, in a computer memory; and
displaying the first visualization and the second visualization of the postoperative face of the patient through a Visualization module, as updated in real time, in a manner which allows a user to select one of the first and the second visualization.

3. The computing system of claim 2 wherein:
the preoperative face of the patient is continually scanned to update said facial recognition Input Data captured by the facial recognition system to thereby update in real-time the first visualization and the second visualization of the postoperative face of the patient.

4. The computing system of claim 2 wherein:
the at least one computer processor is configured to enable the user to modify the first procedure plan; and
wherein the at least one computer processor is configured to generate a modified visualization of the first visualization of the postoperative face of the patient in computer memory based on modification of the first procedure plan by the user.

5. The computing system of claim 4 wherein:
the first procedure plan includes surgical markings;
wherein the at least one computer processor is configured to generate a visualization of the preoperative face of the patient with surgical markings shown overlaid on top of the preoperative face of the patient by use of the AI Engine module;
wherein modification of the first procedure plan by the user include modification to the surgical markings.

6. The computing system of claim 2 wherein:
the first procedure plan includes surgical markings.

7. The computing system of claim 6 wherein:
the at least one computer processor is configured to generate a visualization of a preoperative face of the patient with generated surgical markings shown overlaid on top of the preoperative face of the patient by use of the AI Engine module.

8. The computing system of claim 2 wherein:
after the step of generating the first visualization of the postoperative face of the patient, the at least one computer processor is configured to enable the user to modify the postoperative face of the patient; and
wherein the at least one computer processor is configured to generate a modified procedure plan, which is a modification of the first procedure plan, based on the modification of the postoperative face of the patient.

9. The computing system of claim 1, wherein
the computer memory that stores instructions, includes instructions that, when executed by the at least one computer processor, causes the at least one computer processor to perform operations, including:

receiving facial recognition Input Data for a preoperative face of a patient in real-time, said facial recognition Input Data captured by a facial recognition system, said facial recognition Input Data including changes based on movement of the patient;

using the AI Engine module to process the facial recognition Input Data;

using the AI Engine module to generate the first procedure plan based on the facial recognition Input Data;

generating the first visualization of a postoperative face of the patient as predicted by the AI Engine module based on the facial recognition Input Data and the first procedure plan generated by the AI Engine module, wherein the first visualization is updated in real time based on movement of the patient;

storing the first visualization of the postoperative face of the patient, as updated in real time, in a computer memory;

displaying the first visualization of the postoperative face of the patient, as updated in real time, through a Visualization module; and physically marking the preoperative face of the patient by use of a marking device to mark the first procedure plan on the patient's face.

10. The computing system of claim 1, wherein
the computer memory that stores instructions, includes instructions that, when executed by the at least one computer processor, causes the at least one computer processor to perform operations, including:

receiving facial recognition Input Data for a preoperative face of a patient in real-time, said facial recognition Input Data captured by a facial recognition system, said facial recognition Input Data including changes based on movement of the patient;

using the AI Engine module to process the facial recognition Input Data;

using the AI Engine module to generate the first procedure plan based on the facial recognition Input Data;

generating the first visualization of a postoperative face of the patient as predicted by the AI Engine module based on the facial recognition Input Data and the first procedure plan generated by the AI Engine module, wherein the first visualization is updated in real time based on movement of the patient;

storing the first visualization of the postoperative face of the patient, as updated in real time, in a computer memory;

displaying the first visualization of the postoperative face of the patient, as updated in real time, through the Visualization module; and wherein the AI Engine module processes the facial recognition Input Data captured by the facial recognition system to determine a set of demographics data for the patient;

and wherein the AI Engine module uses the set of demographics data to generate the first procedure plan.

11. The computing system of claim 1, wherein
the computer memory that stores instructions, includes instructions, that, when executed by the at least one computer processor, causes the at least one computer processor to perform operations, including:

receiving facial recognition Input Data for a preoperative face of a patient in real-time, said facial recognition Input Data captured by a facial recognition system, said facial recognition Input Data including changes based on movement of the patient;

using the AI Engine module to process the facial recognition Input Data;

using the AI Engine module to generate the first procedure plan based on the facial recognition Input Data;

generating the first visualization of the postoperative patient's face as predicted by the AI Engine module based on the facial recognition Input Data and the first procedure plan generated by the AI Engine module, wherein the first visualization is updated in real time based on movement of the patient;

storing the first visualization of the postoperative face of the patient, as updated in real time, in a computer memory;

displaying the first visualization of the postoperative patient's face of the patient, as updated in real time, through a Visualization module; and wherein the AI Engine module processes the facial recognition Input Data captured by the facial recognition system to determine medical history for the patient;

and wherein the AI Engine module uses the medical history for the patient to generate the first procedure plan.

12. The computing system of claim 1,
wherein the postoperative feedback includes postoperative results programmed to be uploaded to the AI Engine module at predefined time intervals.

13. The computing system of claim 1, wherein
the computer memory that stores instructions, includes instructions that, when executed by the at least one computer processor, causes the at least one computer processor to perform operations, including:

physically marking in ink on a physical face of the patient by use of a marking device, without user intervention, to mark in ink the first procedure plan on the physical face of the patient.

* * * * *